United States Patent [19]

Delarge et al.

[11] E Re. 30,633

[45] Reissued Jun. 2, 1981

[54] 3-LOWER ALKYLCARBAMYLSULFONAMIDO-4-PHENYLAMINOPYRIDINES, N-OXIDES, DERIVATIVES THEREOF AND PHARMACEUTICAL COMPOSITIONS CONTAINING SAME

[75] Inventors: Jacques E. Delarge, Dolembreux; Charles L. Lapière, Tongeren; André H. Georges, Ottignies, all of Belgium

[73] Assignee: A. Christiaens Societe Anonyme, Brussels, Belgium

[21] Appl. No.: 119,601

[22] Filed: Feb. 7, 1980

Related U.S. Patent Documents

Reissue of:

[64] Patent No.: 4,018,929
Issued: Apr. 19, 1977
Appl. No.: 568,759
Filed: Apr. 16, 1975

U.S. Applications:

[63] Continuation of Ser. No. 31,101, Apr. 18, 1979, abandoned.

[30] Foreign Application Priority Data

Apr. 17, 1974 [GB] United Kingdom ..... 16836/74

[51] Int. Cl.[3] ..... C07D 213/74; A61K 31/44

[52] U.S. Cl. ..... 424/263; 546/291; 546/294

[58] Field of Search ..... 546/291, 294; 424/263

[56] References Cited

U.S. PATENT DOCUMENTS

| | | | |
|---|---|---|---|
| 3,674,794 | 7/1972 | Mizzoni et al. | 546/293 |
| 3,819,639 | 6/1974 | Delarge et al. | 546/293 |
| 3,904,636 | 9/1975 | Delarge et al. | 546/291 |

*Primary Examiner*—Alan L. Rotman
*Attorney, Agent, or Firm*—Sughrue, Rothwell, Mion, Zinn and Macpeak

[57] ABSTRACT

This invention relates to new derivatives of pyridine having anti-inflammatory and diuretic properties.

The new derivatives of pyridine may be represented by the following general formula:

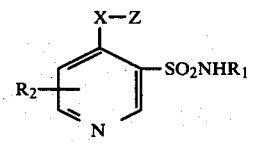

(1).

in which X represents an amino, $C_1$-$C_4$-alkylamino, oxy or thio group, $R_1$ represents a group of the formula $R_3NHCA$ (II), wherein A represents oxygen or sulfur, and $R_3$ represents a $C_1$-$C_4$-alkyl, alkenyl, cycloalkyl, phenyl (which may be substituted) or $R_4CO$ (III) group, $R_4$ representing a phenyl group (which may be substituted), $R_2$ represents hydrogen or a $C_1$-$C_4$ alkyl group and Z represents a $C_1$-$C_4$-alkyl, methylfuryl, pyridyl or phenyl group (which may be substituted).

This invention relates also to the N-oxides of the compounds of formula I, as well as to the acid and base addition salts of said compounds.

9 Claims, No Drawings

3-LOWER ALKYLCARBAMYLSULFONAMIDO-4-PHENYLAMINOPYRIDINES, N-OXIDES, DERIVATIVES THEREOF AND PHARMACEUTICAL COMPOSITIONS CONTAINING SAME

Matter enclosed in heavy brackets [ ] appears in the original patent but forms no part of this reissue specification; matter printed in italics indicates the additions made by reissue.

*This application is a Continuation of Re-issue application, Ser. No. 031,101 filed 4-18-79, now abandoned, which in turn is a Re-issue application of U.S. Pat. No. 4,018,929 issued 4-19-77.*

BRIEF DESCRIPTION OF THE INVENTION

This invention relates to new derivatives of pyridine, their preparation and use.

The new derivatives of pyridine are of the following general formula:

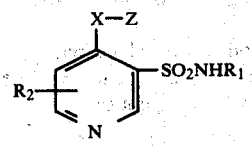

(I).

in which

X represents an amino, $C_1$–$C_4$-alkylamino, oxy or thio group;

$R_1$ represents a group of the formula:

$$R_3NHCA \quad \text{(II)},$$

wherein A represents oxygen or sulfur and $R_3$ represents a $C_1$–$C_4$-alkyl, alkenyl, cycloalkyl or phenyl group, the latter being possibly substituted, or a group of the formula $R_4CO$ (III), wherein $R_4$ represents a phenyl group which may be substituted;

$R_2$ represents hydrogen or a $C_1$–$C_4$-alkyl group, and Z represents a $C_1$–$C_4$-alkyl, methylfuryl, pyridyl or phenyl group, the phenyl group being possibly substituted by one or more substituents selected from the $C_1$–$C_4$-alkyl, alkoxy, halo, trifluoromethyl, nitro groups, with the provisos that:

1. when X represents an amino group, Z, $R_1$, $R_2$, $R_3$ and $R_4$ may have all the above indicated meanings;
2. when X represents an oxy or thio group, Z may only represent a phenyl group as defined hereabove;
3. when X represents an alkylamino group, Z may only represent a $C_1$-$C_4$-alkyl group or a phenyl group as defined hereabove and $R_1$ may further represent a group of the formula:

$$R_5CO \quad \text{(IV)},$$

in which $R_5$ represents hydrogen or a $C_1$–$C_4$-alkyl group;

4. when X represents an amino group and Z is other than a phenyl group, or when X represents an oxy or thio group, $R_1$ may further represent hydrogen or a group of the formula (IV) as above defined.

When, in the compounds of formula I, X represents an imino group, Z a phenyl group and $R_1$ a group of formula III, this invention relates to the cyclization products of the formula:

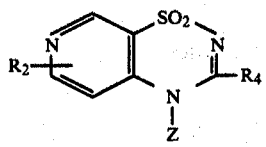

(V), in which $R_2$ and $R_4$ have the above meanings, said cyclization products being obtained spontaneously together with the compounds of formula I, in which X, Z and $R_1$ have the meanings given in this paragraph.

The invention also relates to the N-oxides of the compounds of formula I in which the oxygen atom is attached to the nitrogen atom of the pyridin, and to the base and acid addition salts of said compounds of formulae I and V.

DETAILED DESCRIPTION OF THE INVENTION

The compounds according to this invention, i.e. the compounds of formulae I and V, may be prepared by various processes:

FIRST PROCESS

When it is desired to obtain a compound of formula I, wherein $R_1$ represents a $R_3NHCA$ group as defined above, the process comprises reacting a compound of the following fomula:

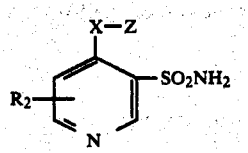

(VI)

with an isocyanate or isothiocyanate of the formula:

$$R_3N{=}C{=}A \quad \text{(VII)},$$

in which Z, $R_2$, $R_3$ and A have the above meanings.

SECOND PROCESS

When it is desired to obtain a compound of formula I, wherein $R_1$ represents a $R_3NHCO$ group as defined above, the process comprises reacting a compound of formula VI with an alkylhaloformate of the formula:

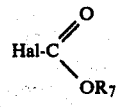

(VIII), in which $R_7$ represents a $C_1$–$C_4$-alkyl group and Hal represents an halogen atom, and an amine of the formula:

$$R_3NH_2 \quad \text{(IX)},$$

in which $R_3$ has the above meanings.

THIRD PROCESS

When it is desired to obtain a compound of formula I, wherein $R_1$ represents a $R_3NHCA$ group as defined above and X represents an imino or alkylimino group, the process comprises reacting a compound of the formula:

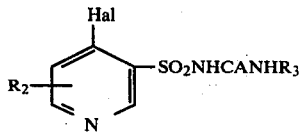

(X), with an amine of the formula:

$R_8—NH—Z$ (XI), wherein $R_8$ represents hydrogen (or a $C_1$–$C_4$-alkyl group, $R_2$, Hal, $R_3$ and Z having the above meanings.

FOURTH PROCESS

When it is desired to obtain a compound of formula I, wherein Z represents a phenyl group which may be substituted in the manner defined above, $R_1$ represents hydrogen or a $R_3NHCA$ group as above defined or a $R_4CO$ or $R_5CO$ group as above defined and X represents a thio or oxy group, the process comprises reacting a compound of the formula:

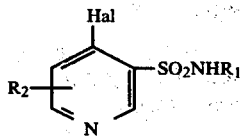

(XII), with a phenolate or thiophenolate of the formula:

Na—X—Z (XIII).

FIFTH PROCESS

When it is desired to obtain a compound of formula I, wherein $R_1$ represents a $R_4CO$ or $R_5CO$ group as defined above, or a compound of formula V, the process comprises reacting a compound of VI with an anhydride of an alkane-carboxylic acid of the formula:

$(R_4—CO)_2O$ or $(R_5—CO)_2O$ (XIV)

or with a chloride of an alkane-carboxylic acid of the formula:

$R_4COCl$ or $R_5CoCl$ (XV).

SIXTH PROCESS

When it is desired to obtain a compound of formula I, in which X, Z and $R_2$ have the above meanings and $R_1$ represents $R_3NHCO$, the process comprises heating a compound of formula I, in which $R_1$ represents a $R_3NHCS$ group, in an aqueous-alcoholic solution of sodium carbonate with an excess of HgO.

SEVENTH PROCESS

When it is desired to obtain the N-oxides of the compounds of formula I, the above processes are applied, except that the corresponding N-oxides of the starting pyridine derivatives are used.

EIGHTH PROCESS

When it is desired to obtain the N-oxides of the compounds of formula I, the process comprises treating a compound of formula I with meta-chloroperoxy-benzoic acid.

The compounds of formula VI, which are used as starting material in the first and sixth processes, may be prepared by the fourth above-described process or by reacting an aliphatic amine with a 4-halogeno-pyridine sulfonamide according to the third above-described process.

It has been found that the compounds of formulae I and V have anti-inflammatory and diuretic properties.

These properties have been determined by the following tests.

1. Pharmacological test for anti-inflammatory properties.

The compounds to be tested are given as freshly prepared solutions or suspensions by oral route 1 hour before injecting the paw of rats with carrageenan which is a known inflammatory agent.

The inflammatory agent (carrageenan) either in solution or suspension is then injected into the plantar tissue of the right hind paw of each rat, the left paw remaining untreated and serving as control. Each animal receives, for example, 0.05 ml of an aqueous solution containing 1% by weight of carrageenan and 0.9% of sodium chloride.

4 hours after the injection of the inflammatory agent, the importance of swelling is determined by plethysmography and is expressed as a percent of the volume of the control paw.

The anti-inflammatory effect expressed as a percentage of inhibition is obtained by comparison between rats treated with the anti-inflammatory compound and a control group of rats.

2. Pharmacological tests for diuretic properties

Lots of 3 rats weighting 250–300 g have been constituted at random, each of them being submitted to the same treatment.

The compound to be tested was administered by [gastric gavage at a dose of 50 ml/kg as a solution or a] *gastric gavage at a dose of 50 mg/kg as a solution or a* suspension in water containing 0.45% of methylcellulose (which is an inert mucilaginous substance). Control animals received only distilled water as a placebo. At the same time, all the animals received 25 ml/kg of physiological saline by subcutaneous injection.

The rats were then placed in metabolic cages, each cage containing 3 animals receiving the same treatment. The urines have been collected during 4 hours.

The increase of urine volume in the treated animals compared with the urine volume of the control animals shows the diuretic action. The diuresis is expressed in ml/kg of body weight.

The results of the tests made with a great number of compounds according to this invention are given in the following table.

TABLE

| Compounds | | Pharmacological properties | |
|---|---|---|---|
| Code Number | Example | Diuresis ml/kg | % inhibition of acute oedema |
| C 2129 | 11 | 30.3 | 23.2 |
| JDL 181 | 77 | 14.8 | 21.6 |
| 344 | 1 | 66.9 | 82.4 |
| 346 | 11(+) | 15.3 | 53.6 |
| 355 | 2 | 57.0 | 48.8 |
| 356 | 22 | 54.7 | 80.8 |
| 357 | 24 | 11.2 | 52.0 |
| 358 | 5 | 17.9 | 57.3 |
| 360 | 6 | 5.2 | 33.6 |

TABLE-continued

| Compounds | | Pharmacological properties | |
|---|---|---|---|
| Code Number | Example | Diuresis ml/kg | % inhibition of acute oedema |
| 361 | 7 | 9.6 | 56.8 |
| 362 | 8 | 8.1 | 37.6 |
| 363 | 14 | 40.1 | 63.2 |
| 364 | 3 | 37.7 | 58.4 |
| 365 | 10 | 8.7 | 43.2 |
| 366 | 9 | 11.1 | 56.0 |
| 367 | 23 | 11.1 | 80.0 |
| 368 | 4 | 6.1 | 57.0 |
| 375 | 36 | 80.5 | 46.4 |
| 378 | 19 | 84.0 | 74.4 |
| 379 | 34 | 76.5 | 63.2 |
| 383 | 18 | 57.8 | 55.2 |
| 384 | 85 | 12.8 | 66.4 |
| 385 | 86 | 17.6 | 46.6 |
| 386 | 20 | 80.5 | 80.8 |
| 387 | 35 | 80.9 | 76.8 |
| 388 | 38 | 37.0 | 66.4 |
| 389 | 39 | 73.3 | 64.0 |
| 390 | 40 | 16.9 | 47.2 |
| 391 | 41 | 9.6 | 74.4 |
| 402 | 27 | 65.4 | 76.8 |
| 403 | 28 | 74.9 | 76.8 |
| 404 | 29 | 43.1 | 76.8 |
| 413 | 37 | 92.5 | 76.8 |
| 414 | 21 | 82.9 | 75.2 |
| 415 | 47 | 47.0 | 75.2 |
| 416 | 48 | 52.8 | 85.6 |
| 417 | 49 | 58.3 | 72.8 |
| 420 | 26 | 65.0 | 52.8 |
| 421 | 30 | 72.0 | 88.8 |
| 422 | 31 | 56.7 | 46.4 |
| 423 | 50 | 68.7 | 64.0 |
| 424 | 51 | 21.0 | 50.4 |
| 425 | 52 | 37.7 | 42.4 |
| 426 | 53 | 22.0 | 73.6 |
| 427 | 32 | 11.4 | 53.6 |
| 428 | 33 | 15.6 | 17.6 |
| 463 | 70 | 76.1 | 73.6 |
| 464 | 71 | 81.6 | 76.8 |
| 465 | 58 | 76.7 | 71.2 |
| 466 | 59 | 70.7 | 68.0 |
| 467 | 55 | 65.8 | 69.6 |
| 468 | 56 | 77.2 | 72.0 |
| 469 | 67 | 46.9 | 60.8 |
| 470 | 68 | 74.9 | 83.2 |
| 471 | 78 | 37.7 | 70.4 |
| 472 | 79 | 69.6 | 54.4 |
| 473 | 62 | 24.0 | 41.6 |
| 474 | 63 | 33.3 | — |
| 475 | 60 | 34.3 | 79.2 |
| 476 | 61 | 42.1 | 92.0 |
| 477 | 44 | 43.6 | 61.6 |
| 478 | 45 | 29.7 | 29.6 |
| 479 | 46 | 44.3 | 45.6 |
| 480 | 12 | 26.4 | 65.6 |
| 482 | 14 | 25.3 | 0 |
| 483 | 83 | 12.4 | 0 |
| 484 | 82 | 9.0 | 13.6 |
| 485 | 80 | 51.3 | 15.2 |
| 486 | 76 | 3.6 | 16.8 |
| 487 | 75 | 10.5 | 20.8 |
| 488 | 74 | 16.4 | 24.8 |
| 491 | 84 | 25.1 | 88.0 |
| 492 | 15 | 14.9 | 88.8 |
| 493 | 66 | 50.7 | 59.2 |
| 494 | 69 | 75.9 | 85.6 |
| 495 | 57 | 76.3 | 66.2 |
| 496 | 54 | 72.1 | 70.4 |
| 501 | | 35.9 | 39.2 |
| 502 | 16 | 43.8 | 1.6 |
| 503 | 43 | 48.9 | 71.2 |
| 504 | 64 | 17.2 | 43.0 |
| 505 | 65 | 56.3 | 68.0 |
| 506 | 81 | 13.5 | — |
| 509 | 25 | [106.4] *34* | — |
| 510 | 16(+) | [92.5] *42* | — |
| 511 | 72 | 66.4 | 72.0 |
| 512 | 73 | 65.9 | 78.7 |

(+) = N-oxide.

This invention relates therefore also to pharmaceutical compositions containing as active ingredient at least one compound of the formula I or V, or a N-oxide or such a compound or a base- or acid-addition salt thereof, together with a pharmaceutically acceptable vehicle or carrier.

The compounds of this invention may be administered in the form of dragees, tablets, capsules and suppositories at daily doses of 50 to 300 mg of active compound.

EXAMPLES

The following examples illustrate the preparation of compounds of formulae I and V.

EXAMPLE 1

Preparation of 3-butylcarbamylsulfonamido-4-(3'-chloro)-phenylaminopyridine (formula I: Z=1-chlorophenyl; $R_1$=$CONHC_4H_9$; $R_2$=H and X=NH).

A. FIRST PROCESS 3-sulfonamido-4-(3'-chloro)-phenylaminopyridine (0.02 mole) is reacted with n-butylisocyanate (0.025 mole) in the presence of 1 to 2 ml of triethylamine by heating at 85°-95° C. during 10 hours. The residue is taken up with alcohol (30 ml) and NaOH 2 N, acidified by means of acetic acid and then diluted with an excess of water which gives a precipitate. The mixture is treated with a 5% solution of sodium bicarbonate in a mixture (3:1) of water and alcohol during 1 hour, then filtered and acidified, whereby the desired product precipitates.

B. SECOND PROCESS

The same product is obtained by reacting in acetone a mixture of ethyl chloroformate (0.06 mole), 3-sulfonamido-4-(3'-chloro)-phenylaminopyridine (0.05 mole) and potassium carbonate (8.5 g), by reflux heating with stirring for 2 hours. The acetone is distilled off and the residue is poured into an excess of water which is acidified by means of hydrochloric acid. The product which appears is extracted with ether, the ether is dried and then distilled to give a residue which is dissolved in diethoxyethane or propylene glycol (10 ml), to which butyl-amine (0.02 mole) is added, the resulting mixture being reflux heated during 15 hours, diluted with 100 ml of water and acidified by means of acetic acid. After precipitation, the product is purified with sodium bicarbonate and recovered as described in part A of this example.

C. THIRD PROCESS 3-butylcarbamylsulfonamide-4-chloropyridine (0.01 mole) and metachloroaniline (0.0125 mole) and copper powder are mixed intimately and heated carefully until the temperature spontaneously rises. The resulting reaction mixture is cooled and the product is purified and isolated as in part A of this example.

Whenever prepared by one of the above described methods, the product is in the form of white crystals, m.p. 139°-140° C.

EXAMPLE 2

Preparation of 3-propylcarbamylsulfonamido-4-(3'-trifluoromethyl)-phenylaminopyridine (formula I: Z=trifluoromethylphenyl; $R_1=CONHC_3H_7$; $R_2=H$ and X=NH).

This product is prepared by the methods described in parts A and C of Example 1, using each time the appropriate starting materials. White crystals; m.p. 166°-168° C.

EXAMPLE 3

Preparation of 3-cyclohexylcarbamylsulfonamido-4-(3'-trifluoromethyl)-phenylaminopyridine (formula I: Z=trifluoromethylphenyl; $R_1=CONHC_6H_{11}$; $R_2=H$ and X=NH).

This product is prepared by the methods described in parts A and C or Example 1, using each time the appropriate starting materials. White crystals; m.p. 126°-128° C.

EXAMPLE 4

Preparation of 3-phenylcarbamylsulfonamido-4-(3'-trifluoromethyl)-phenylaminopyridine (formula I: Z=trifluoromethylphenyl;

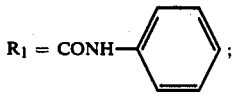

$R_2=H$ and X=NH).

Using the method described in part A of Example 1, one obtains white crystals; m.p. 180°-182° C.

EXAMPLE 5

Preparation of 3-propionylsulfonamido-4-(N-methylanilino)-pyridine (formula I: Z=phenyl, $R_1=COC_2H_5$; $R_2=H$ and $X=N—CH_3$).

The following mixture:

0.01 mole of 3-sulfonamido-4-(N-methylanilino)-pyridine 10 ml of propionyl chloride or anhydride 10 ml of pyridine is reacted during 12 hours (fifth process).

The reacted mixture is poured into an excess of 10% NaOH, filtered whenever necessary and acidified by means of acetic acid which gives a precipitate. The precipitate is dissolved in 100 ml of 5% sodium bicarbonate in a mixture of water and alcohol (3:1). The mixture thus obtained is filtered and the filtrate is acidified to give the desired product as a yellowish white product, m.p. 247° C.

EXAMPLE 6

Preparation of 3-sulfonamido-4-(3'-chloro)-phenoxypyridine (formula I: Z=chlorophenyl; $R_1=H$; $R_2=H$ and X=O).

Fourth process—a mixture of 3-sulfonamido-4-chloropyridine (0.02 mole), sodium meta-chlorophenolate (0.04 mole) and meta-chlorophenol (0.02 mole) is heated and maintained at about 160°-180° C. during ½ hour. The mixture is taken up with 100 ml of alcohol, acidified by means of acetic acid and diluted with water. The desired product precipitates; m.p. 161°-163° C. (white crystals).

EXAMPLE 7

Preparation of 3-sulfonamido-4-(3'-chloro)-thiophenoxypyridine (formula I: Z=chlorophenyl; $R_1=H$; $R_2=H$ and X=S).

Fourth process—the following mixture is allowed to boil during 1 hour: 0.02 mole of 3-sulfonamido-4-chloropyridine and 0.03 mole of sodium metachlorothiophenolate. The mixture is diluted with an excess of water and acidified with acetic acid. The product crystallizes as white crystals; m.p. 150°-152° C.

EXAMPLE 8

Preparation of 3-acetylsulfonamido-4-(3-chloro)-thiophenoxy-pyridine (formula I: Z=chlorophenyl, $R_1=COCH_3$; $R_2=H$ and X=S).

A. FIFTH PROCESS 3-sulfonamido-4-(3'-chloro)-thiophenoxypyridine (5 g) is contacted with pyridine (25 ml) and acetic anhydride (25 ml) during 3 hours. The reacted mixture is poured into an excess of 10% NaOH, filtered if necessary and acidified by means of acetic acid. The product is separated, purified by dissolution in 200 ml of 5% $NaHCO_3$ in a mixture of water and alcohol (3:1) and again precipitated by means of acetic acid.

B. FOURTH PROCESS 3-acetylsulfonamido-4-chloropyridine (0.01 mole) and sodium metachlorothiophenolate (0.01 mole) and absolute ethanol (100 ml) are reflux heated during 1 hour. After distillation of 50 ml of ethanol, the mixture is diluted with an excess of water, giving a precipitate which is purified and isolated as in part A of this example. White product; m.p. 229°-230° C.

EXAMPLE 9

Preparation of 3-butylcarbamylsulfonamido-4-(3'-chloro)-thiophenoxypyridine (formula I: Z=chlorophenyl; $R_1=CONHC_4H_9$; $R_2=H$ and X=S).

A. The desired product is obtained from 3-sulfonamido-4-(3'-chloro)-thiophenoxypyridine as described in part A of Example 1.

B. The same product is also obtained by the fourth process using sodium metachlorothiophenolate and absolute ethanol as a diluent.

In both instances, one obtains a white product; m.p. 195°-197° C.

EXAMPLE 10

Preparation of
3-propylcarbamylsulfonamido-4-(3'-chloro)-phenoxypyridine (formula I: Z=chlorophenyl; $R_1$=$CONHC_3H_7$; $R_2$=H and X=O).

First process—3-sulfonamido-4-(3'-chloro)-phenoxypyridine (0.01 mole) is intimately mixed with propylisocyanate (0.0125 mole) and triethylamine (0.5–1 ml). The mixture thus obtained is maintained 4 hours at 85°–95° C., taken up with 50 ml of alcohol and a few ml of NaOH 2 N, heated to dissolve any soluble matter, acidified with acetic acid 300 ml of water are then added thereto. The product is purified and isolated as described previously, using a solution of $NaHCO_3$ to give small white crystals; m.p. 177°–179° C.

EXAMPLE 11

Preparation of
3-benzoylsulfonamido-4-(3'-trifluoromethyl)-phenylaminopyridine and
3-phenyl-4-metatrifluoromethyl-4H-pyridino-[4,3-e]-1,2,4-thiadiazine-1,1-dioxide (formulae I and V: Z=trifluoromethyl-phenyl;

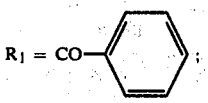

$R_2$=H; $R_4$=phenyl and X=NH).

A. 0.01 mole of 3-sulfonamido-4-(3-trifluoromethyl)-phenylaminopyridine, 0.030 mole of benzoyl chloride and 20 ml of anhydrous pyridine are left in contact with one another for 24 hours. The resulting mixture is poured into NaOH (10%). One obtains a precipitate of the cyclized second title product (m.p. 290° C.) and a solution. When neutralized by acetic acid, the solution gives a precipitate of impure first title compound. Said precipitate is stirred with an aqueous solution of $NaHCO_3$ to extract the little amount of benzoic acid contained therein. It is then treated with a water-alcohol solution of $NaHCO_3$, dissolved, the resulting solution is filtered and neutralized by means of acetic acid. The desired first title compound precipitates (m.p. 249° C.). By treatment with a dehydrating agent, such as acetic anhydride, the first title compound is converted into the second title compound.

B. A mixture of 0.01 mole of 4-chloro-3-benzoylsulfonamido-pyridine, 0.01 mole of meta-trifluoromethylaniline and a little amount of copper powder is heated at about 80° C. A spontaneous heating occurs. The mixture is maintained during 10 minutes at about 80°–100° C. and is then taken up with water and adjusted to a pH of 5. The precipitate is treated as described in part A of this example, using a water-alcoholic solution of sodium bicarbonate, filtered and neutralized by means of acetic acid. The first title compound crystallizes (m.p. 249° C.). By treatment of this compound using acetic anhydride, the first title compound cyclizes to form the second title compound (m.p. 290° C.).

EXAMPLE 12

Preparation of
3-allyl-thiocarbamyl-sulfonamido-4-(3'-chloro)-phenylaminopyridine (formula I: Z=chlorophenyl; $R_1$=allyl-thiocarbamyl; $R_2$=H and X=NH).

In a mixture of equal parts of water and dioxane, 0.01 mole of sodium salt of 3-sulfonamido-4-(3'-chloro)-phenylaminopyridine is dissolved and 0.02 mole of allylisothiocyanate is added little by little.

The reaction mixture is maintained 1 hour at 50° C. under stirring, then diluted by 250 ml of water and acidified.

The crude product is purified by dissolution in a water-alcohol solution of $NaHCO_3$ and back-precipitation by means of acetic acid; (m.p. 175°–177° C.).

EXAMPLE 13

Preparation of
3-allylcarbamylsulfonamido-4-(3'-chloro)-phenylaminopyridine (formula I: Z=chlorophenyl; $R_1$=allylcarbamyl; $R_2$=H; X=NH).

SIXTH PROCESS 0.01 mole of 3-allylthiocarbamylsulfonamido-4-(3'-chloro)-phenylaminopyridine is dissolved in 100 ml of water and 5 g of $Na_2CO_3$. One adds 10 g of HgO and one heats and maintains the reaction mixture under reflux conditions until all the sulphur is removed as HgS. Said mixture is filtrated and its pH is adjusted to 4–5. The product precipitates. It is purified by dissolution in $NaHCO_3$ and back precipitation (m.p. 161°–163° C.).

EXAMPLE 14

Preparation of
3-isopropylcarbamylsulfonamido-4-isopropylaminopyridine (formula I: Z=isopropyl; $R_1$=isopropylcarbamyl; $R_2$=H and X=NH).

By reacting the appropriate products as described in any of examples 1A, B or C, one obtains the desired title compound.

When applying the process of Example 1C, the reactants are preferably heated to 120° C. in a closed reaction vessel. Alternatively, an intermediate solvent such as propyleneglycol is used (m.p. 193° C.).

EXAMPLE 15

Preparation of
3-methylcarbamylsulfonamido-4-methylfurylaminopyridine (formula I: Z=methylfuryl); $R_1$=methylcarbamyl; $R_2$=H and X=NH).

This product is conveniently prepared by applying any of the processes described in Examples 1A and 1C with very good results; m.p. 208°–209° C.

EXAMPLE 16

Preparation of
3-isopropylcarbamylsulfonamido-4-(3'-methyl)-phenylaminopyridine-N-oxide (formula I: Z=methylphenyl; $R_1$=isopropylcarbamyl; X=NH).

1. SEVENTH PROCESS 4-chlorosulfonamidopyridine-N-oxide (m.p. 217°–219° C.) is first condensed with toluidine using the usual method. 0.01 mole of the 3-sulfonamido-4-(3'-methyl)-phenylaminopyridine-N-oxide thus obtained is reacted, in the form of its sodium salt, with 0.011 mole of isopropylisocyanate in 50 ml of a (1:1) water-dioxane mixture for 1 hour at about 40° C. The mixture is diluted with 250 ml of water and adjusted to pH 4–5. The crude product is purified by dissolution in a water-alcohol (3:1) solution of $NaHCO_3$ and back precipitation by means of HOAC.

2. EIGHTH PROCESS 0.01 mole of 3-isopropylcarbamylsulfonamido-4(3'-methyl)-phenylaminopyridine is dissolved in 150 ml of $CHCl_3$. 0.01 mole of metachloroperoxybenzoic acid is slowly added drop by drop under good stirring and the reaction is allowed to proceed for a few hours under cool conditions. $CHCl_3$ is evaporated and the residue is taken up with ether. The insoluble matter, mainly consisting of the crude product, is purified by the usual $NaHCO_3$ treatment; [(m.p. 158° C).] *(m.p. 180°–181° C.).*

EXAMPLE 17

Preparation of 3-ethylcarbamylsulfonamido-4-(3'-chloro)-phenylamino-5-methylpyridine (formula I:Z=chlorophenyl; $R_1$=ethylcarbamyl; $R_2$=methyl; X=NH). (m.p. 182° C.).

This compound is obtained by any one of the methods described in Example 1. It is however preferred to apply the method of Example 1A using as starting materials ethyl isocyanate and 3-sulfonamido-4-(3'-chloro)-phenylamino-5-methylpyridine (m.p. 251° C.).

EXAMPLES 18–92

Applying any of the above-described methods, the following compounds listed in the table hereinafter are prepared. Unless otherwise specified, all these products are white crystals, sparingly soluble in water, more soluble in alcohol and acetone, soluble in the bases except the second title compound of Example 11, and concentrated inorganic acids.

| Compounds of Ex. | Code N° | Name and melting point of compound |
|---|---|---|
| 18 | JDL 383 | 3-pripylcarbamylsulfonamido-4-N-methyl-anilinopyridine (formula I : Z = phenyl; $R_1$ = Methylcarbamyl; $R_2$ = H and X = $NcH_3$); m.p. 105–107° C. |
| 19 | JDL 378 | 3-methylcarbamylsulfonamido-4-(3'-trifluoromethyl)-phenylaminopyridine (formula I : 2 = trifluoromethylphenyl; $R_1$ = methylcarbamyl; $R_2$ = H and X = NH); m.p. 189–191° C. |
| 20 | JDL 386 | 3-ethylcarbamylsulfonamido-4-(3'-trifluoromethyl)-phenylaminopyridline (formula I : Z = trifluorothyphenyl; $R_1$ = ethylcarbamyl; $R_1$ = H and X = NH); m.p. 164–165° C. |
| 21 | JDL 414 | 3-isopropylcarbamylsulfonamido-4-(3'-trifluoromethyl)-phenylaminopyridine (formula I : Z = trifluoromethylphenyl; $R_1$ = isopropylcarbamyl; $R_2$ = H and X = NH); m.p. 177° C. |
| 22 | JDL 356 | 3-butylcarbamylsulfonamido-4-(3'-trifluoromethyl)-phenylaminopyridine (formula I : Z = trifluoromethylphenyl; $R_1$ = butylcarbamyl; $R_2$ = H and X = NH); m.p. 150–152° C. |
| 23 | JDL 367 | 3-tertbutylcarbamylsulfonamido-4-(3'-trifluoromethyl)-phenylaminopyridine (formula I : Z = trifluoromethylphenyl; $R_1$ = t-butylcarbamyl; $R_2$ = H and X = NH); m.p. 168–170° C. |
| 24 | JDL 357 | 3-parachlorophenylcarbamylsulfonamido-4-(3'-trifluoromethyl)-phenylaminopyridine (formula I : Z = trifluoromethylphenyl; $R_1$ = para-chlorophenylcarbamyl; $R_2$ = H and X = NH); m.p. 208–210° C. |
| 25 | JDL 509 | 3-ethylcarbamylsulfonamido-4-(3'-trifluoromethyl)-phenylaminopyridine-N-oxide (formula I : Z = trifluoromethylphenyl; $R_1$ = ethylcarbamyl; $R_2$ = H and X = NH); m.p. [163° C.] *123–125° C.* |
| 26 | JDL 420 | 3-ethylthiocarbamylsulfonamido-4-(3'trifluoromethyl)-phenylaminopyridine (formula I : Z = trifluoromethylphenyl; $R_1$ = ethylthiocarbamyl; $R_2$ = H and X = NH); m.p. 178–180° C. |
| 27 | JDL 402 | 3-methylcarbamylsulfonamidio-4-(2'-chloro)-phenylaminopyridine (formula I : Z = chlorophenyl; $R_1$ = methylcarbamyl; $R_2$ = H and X = NH); m.p. 192° C. |
| 28 | JDL 403 | 3-ethylcarbamylsulfonamido-4-(2'-chloro)-phenylaminopyridine (formula I : Z = chlorophenyl; $R_1$ = ethylcarbamyl; $R_1$ = H and X = NH); m.p. 176–178° C. |
| 29 | JDL 404 | 3-propylcarbamylsulfonamido-4-(2'-chloro)-phenylaminopyridine (formula I : Z = chlorophenyl; $R_1$ = propylcarbamyl; $R_2$ = H and X = NH); m.p. 151–152° C. |
| 30 | JDL 421 | 3-isopropylcarbamylsulfonamido-4-(2'-chloro)-phenylaminopyridine (formula I : Z = chlorophenyl; $R_1$ = isopropylcarbamyl; $R_2$ = H and X = NH); m.p. 144° C. |
| 31 | JDL 422 | 3-butylcarbamylsulfonamido-4(2'-chloro)-phenylaminopyridine (formula I : Z = chlorophenyl; $R_1$ = t-butylcarbamyl; $R_2$ = H and X = NH); m.p. 116° C. |
| 32 | JDL 427 | 3-tertiobutylcarbamylsulfonamido-4-(2'-chloro)-phenylaminopyridine (formula I : Z = chlorophenyl; $R_1$ = butylcarbamyl; $R_2$ = H and X = NH); m.p. 185° C. |
| 33 | JDL 428 | 3-cyclohexylcarbamylsulfonamido-4-(2'-chloro)-phenylamionpyridine (formula I : Z = chlorophenyl; $R_1$ = cyclohexylcarbamyl; $R_2$ = H and X = NH); m.p. 137° C. |
| 34 | JDL 379 | 3-methylcarbamylsulfonamido-4-(3'-chloro)-phenylaminopyridine (formula I : Z = chlorophenyl; $R_1$ = methylcarbamyl; $R_2$ = H and X = NH); m.p. 174–176° C. |
| 35 | JDL 387 | 3-ethylcarbamylsulfonamido-4-(3'-chloro-phenylaminopyridine (formula I : Z = chlorophenyl; $R_1$ = ethylcarbamyl; $R_2$ = H and X = NH); m.p. 163–165° C. |
| 36 | JDL 375 | 3-propylcarbamylsulfonamido-4-(3'-chloro)-phenylaminopyridine (formula I : Z = chlorophenyl; $R_1$ = propylcarbamyl; $R_2$ = H and X = NH); m.p. 176° C. |
| 37 | JDL 413 | 3-isopropylcarbamylsulfonamido-4-(3'-chloro)-phenylaminopyridine (formula I : Z = chlorophenyl; $R_1$ = isopropylcarbamyl; $R_2$ = H and X = NH); m.p. 179° C. |
| 38 | JDL 388 | 3-tertiobutylcarbamylsulfonamido-4-(3'-chloro)-phenylaminopyridine (formula I : Z = chlorophenyl; $R_1$ = t-butylcarbamyl; $R_2$ = H; X = NH); m.p. 172–173° C. |

-continued

| Compounds of Ex. | Code N° | Name and melting point of compound |
|---|---|---|
| 39 | JDL 389 | 3-cyclohexylcarbamylsulfonamido-4-(3'-chloro)-phenylaminopyridine (formula I : Z = chlorophenyl; $R_1$ = cyclohexylcarbamyl; $R_2$ = H and X = NH); m.p. 125° C. |
| 40 | JDL 390 | 3-phenylcarbamylsulfonamido-4-(3'-[chloro)-phenylaminopyridine (formu-]*chloro)-phenylaminopyridine (formu*la I : Z = chlorophenyl; $R_1$ = phenylcarbamyl; $R_2$ = H and X = NH); m.p. 214° C. |
| 41 | JDL 391 | 3-parachlorophenylcarbamylsulfonamido-4-(3'-chloro)-phenylaminopyridine (formula I : Z = chlorophenyl; $R_1$ = parachlorophenylcarbamyl; $R_2$ = H and X = NH); m.p. 213–215° C. |
| 42 | JDL 501 | 3-methylcarbamylsulfonamido-4-(3'-chloro)-phenylamino-5-methylpyridine (formula I : Z = chlorophenyl; $R_1$ = methylcarbamyl; $R_2$ = $CH_2$ and X = NH); m.p. 189° C. |
| 43 | JDL 503 | 3-isopropylcarbamylsulfonamido-4-(3'-chloro)-phenylamino-5-methylpyridine (formula I : Z = chlorophenyl; $R_1$ = isopropylcarbamyl-$R_2$ = $CH_3$ and X = NH); m.p. 174° C. |
| 44 | JDL 477 | 3-methylthiocarbamylsulfonamido-4-(3'-chloro)-phenylaminopyridine (formula I : Z = chlorophenyl; $R_1$ = methylthiocarbamyl; $R_2$ = H and X = NH); m.p. 194–195° C. |
| 45 | JDL 478 | 3-ethylthiocarbamylsulfonamido-4-(3'-chloro)-phenylaminopyridine (formula I : Z = chlorophenyl: $R_1$ = ethylthiocarbamyl; $R_2$ = H and X = NH); m.p. 195–196° C. |
| 46 | JDL 479 | 3-isopropylthiocarbamylsulfonamido-4-(3'-chloro)-phenylaminopyridine (formula I : Z = chlorophenyl; $R_1$ = isopropylthiocarbamyl; $R_2$ = H and X = NH); m.p. 189–191° C. |
| 47 | JDL 415 | 3-methylcarbamylsulfonamido-4-(4'-chloro)-phenylaminopyridine (formula I : Z = chlorophenyl; $R_1$ = methylcarbamyl; $R_2$ = H and X = NH); m.p. 180° C. |
| 48 | JDL 416 | 3-ethylcarbamylsulfonamido-4-(4'-chloro)-phenylaminopyridine (formula I : Z = chlorophenyl; $R_1$ = ethylcarbamyl; $R_2$ = H and X = NH); m.p. 201° C. |
| 49 | JDL 417 | 3-propylcarbamylsulfonamido-4-(4'-chloro)-phenylaminopyridine (formula I : Z = chlorophenyl; $R_1$ = propylcarbamyl; $R_2$ = H and X = NH); m.p. 168–170° C. |
| 50 | JDL 423 | 3-isopropylcarbamylsulfonamido-4-(4'-chloro)-phenylaminopyridine (formula I : Z = chlorophenyl; $R_1$ = isopropylcarbamyl; $R_2$ = H and X = NH); m.p. 143° C. |
| 51 | JDL 424 | 3-butylcarbamylsulfonamido-4-(4'-chloro)-phenylaminopyridine (formula I : Z = chlorophenyl; $R_1$ = butylcarbamyl; $R_2$ = H and X = NH); m.p. 170–172° C. |
| 52 | JDL 425 | 3-tertiobutylcarbamylsulfonamido-4-(4'-chloro)-phenylaminopyridine (formula I : Z = chlorophenyl; $R_1$ = t-butylcarbamyl; $R_2$ = H and X = NH); m.p. 118° C. |
| 53 | JDL 426 | 3-cyclohexylcarbamylsulfonamido-4-(4'-chloro)-phenylaminopyridine (formula I : Z = chlorophenyl; $R_1$ = cyclohexylcarbamyl; $R_2$ = H and X = NH); m.p. 178° C. |
| 54 | JDL 496 | 3-methylcarbamylsulfonamido-4-(3'-bromo)-phenylaminopyridine (formula I : Z = bromophenyl; $r_1$ = methylcarbamyl; $R_2$ = H and X = NH); m.p. 187° C. |
| 55 | JDL 467 | 3-ethylcarbamylsulfonamido-4-(3'-bromo)-phenylaminopyridine (formula I : Z = bromophenyl; $R_1$ = ethylcarbamyl; $R_2$ = H and X = NH); m.p. 165–167° C. |
| 56 | JDL 468 | 3-isopropylcarbamylsulfonamido-4-(3'-bromo)-phenylaminopyridine (formula I : Z = bromophenyl; $R_1$ = isopropylcarbamyl; $R_2$ = H and X = NH); m.p. 157–159° C. |
| 57 | JDL 495 | 3-methylcarbamylsulfonamido-4-(3'-fluoro)-phenylaminopyridine (formula I : Z = fluorophenyl; $R_1$ = methylcarbamyl; $R_1$ = H and X = NH); m.p. 170–172° C. |
| 58 | JDL 465 | 3-ethylcarbamylsulfonamido-4-(3'-fluoro)-phenylaminopyridine (formula I : Z = fluorophenyl; $R_1$ = ethylcarbamyl; $R_2$ = H and X = NH); m.p. 158–160° C. |
| 59 | JDL 466 | 3-isopropylcarbamylsulfonamido-4-(3'-fluoro)-phenylaminopyridine (formula I : Z = fluorophenyl; $R_1$ = isopropylcarbamyl; $R_2$ = H and X = NH); m.p. 163–165° C. |
| 60 | JDL 475 | 3-ethylcarbamylsulfonamido-4-(3',4'-dichloro)-phenylaminopyridine (formula I : Z = dichlorophenyl; $R_1$ = ethylcarbamyl; $R_2$ = H and X = NH); m.p. 166–168° C. |
| 61 | JDL 476 | 3-isopropylcarbamylsulfonamido-4-(3',4'-dichloro)-phenylaminopyridine (formula I : Z = dichlorophenyl; $R_1$ = isopropylcarbamyl; $R_2$ = H and X = NH); m.p. 123–125° C. |
| 62 | JDL 473 | 3-ethylcarbamylsulfonamido-4-(3',5'-dichloro)-phenylaminopyridine (formula I : Z = dichlorophenyl; $R_1$ = ethylcarbamyl; $R_2$ = H and X = NH); m.p. 165–167° C. |
| 63 | JDL 474 | 3-isopropylcarbamylsulfonamido-4-(3',5'-dichloro)-phenylaminopyridine (formula I : Z = dichlorophenyl; $R_1$ = isopropylcarbamyl; $R_2$ = H and X = NH); m.p. 124–126° C. |
| 64 | JDL 504 | 3-methylcarbamylsulfonamido-4-(3'-nitro)-phenylaminopyridine (formula I : Z = nitrophenyl; $R_1$ = methylcarbamyl; $R_2$ = H and X = NH); m.p. 173° C. (yellow product) |
| 65 | JDL 505 | 3-isopropylcarbamylsulfonamido-4-(3'-nitro)-phenylaminopyridine (formula I : Z = nitrophenyl; I : 1 = isopropylcarbamyl; $R_2$ = H and X = NH); m.p. 166° C. (yellow product) |
| 66 | JDL 493 | 3-methylcarbamylsulfonamido-4-(3'-methoxy)-phenylaminopyridine (formula I : Z = methoxyphenyl; $R_1$ = methylcarbamyl; $R_2$ = H and X = NH); m.p. 177° C. |
| 67 | JDL 469 | 3-ethylcarbamylsulfonamido-4-(3'-methoxy)-phenylaminopyridine (formula I : Z = methoxyphenyl; $R_1$ = ethylcarbamyl; $R_2$ = H and X = NH); m.p. 99–101° C. |
| 68 | JDL 470 | 3-isopropylcarbamylsulfonamido-4-(3'-methoxy)-phenylaminopyridine (formula I : Z = methoxyphenyl; $R_1$ = isopropylcarbamyl; $R_2$ = H and X = NH); m.p. 144–146° C. |
| 69 | JDL 494 | 3-methylcarbamylsulfonamido-4-(3'-methyl)-phenylaminopyridine (formula I : Z = methylphenyl; $R_1$ = methylcarbamyl; $R_2$ = H and X = NH); m.p. 174° C. |
| 70 | JDL 463 | 3-ethylcarbamylsulfonamido-4-(3'- |

-continued

| Compounds of Ex. | Code N° | Name and melting point of compound |
|---|---|---|
| | | methyl)-phenylaminopyridine (formula I : Z = methylphenyl; $R_1$ = ethylcarbamyl; $R_2$ = H and X = NH); m.p. 151–153° C. |
| 71 | JDL 464 | 3-isopropylcarbamylsulfonamido-4-(3'-methyl)-phenylaminopyridine (formula I : Z = methylphenyl; $R_1$ = isopropylcarbamyl; $R_2$ = and X = NH); m.p. 163–164° C. |
| 72 | JDL 511 | 3-ethylcarbamylsulfonamido-4-(3'-ethyl)-phenylaminopyridine (formula I : Z = ethylphenyl; $R_1$ = ethylcarbamyl; $R_2$ = H and X = NH); m.p. 165° C. |
| 73 | JDL 512 | 3-isopropylcarbamylsulfonamido-4-(3'-ethyl)-phenylaminopyridine (formula I : Z = ethylphenyl; $R_1$ = isopropylcarbamyl; $R_2$ = H and X = NH); m.p. 145° C. |
| 74 | JDL 488 | 3-ethylcarbamylsulfonamido-4-(3'-trifluoromethyl-4'-chloro)-phenylaminopyridine (formula I : Z = trifluoromethyl-chlorophenyl; $R_1$ = ethylcarbamyl; $R_2$ = H and X = NH); m.p. 172° C. |
| 75 | JDL 487 | 3-isopropylcarbamylsulfonamido-4-(3'-trifluoromethyl-4'-chloro)-phenylaminopyridine (formula I : Z = trifluoromethyl-chlorophenyl; $R_1$ = isopropylcarbamyl; $R_2$ = H and X = NH); m.p. 178° C. |
| 76 | JDL 486 | 3-butylcarbamylsulfonamido-4-(3'-trifluoromethyl-4'-chloro)-phenyl aminopyridine (formula I : Z = trifluoromethyl-chlorophenyl; $R_1$ = butylcarbamyl; $R_2$ = H and X = NH); m.p. 128° C. |
| 77 | JDL 181 | 3-sulfonamido-4-methylfurylaminopyridine (formula I : Z = methylpropyl; $R_1$ = H; $R_2$ = H and X = NH); m.p. 160–162° C. |
| 78 | JDL 471 | 3-ethylcarbamylsulfonamido-4-methylfurylaminopyridine (formula I : Z = methylfuryl; $R_2$ = ethylcarbamyl; $R_2$ = H and X = NH); m.p. 183–184° C. |
| 79 | JDL 472 | 3-isopropylcarbamylsulfonamido-4-methylfurylaminopyridine (formula I : Z = methylfuryl; $R_1$ = isopropylcarbamyl; $R_2$ = H and X = NH); m.p. 147–148° C. |
| 80 | JDL 485 | 3-butylcarbamylsufonamido-4-methylfurylaminopyridine (formula I : Z = methylfuryl; $R_1$ = butylcarbamyl; $R_2$ = H and X = NH); m.p. 159° C. |
| 81 | JDL 506 | 3-methylcarbamylsulfonamido-4-(3'-pyridylamino)-pyridine (formula I : Z = pyridyl; $R_1$ = methylcarbamyl; $R_2$ = H and X = NH); m.p. 249° C. |
| 82 | JDL 484 | 3-sulfonamido-4-diethylaminopyridine (formula I : Z = ethyl; $R_1$ = H; $R_2$ = H and X = $NC_2H_5$); m.p. 171° C. |
| 83 | JDL 483 | 3-isopropylcarbamylsulfonamido-4-diethylaminopyridine (formula I : Z = ethyl; $R_1$ = isopropylcarbamyl; $R_2$ = H and X = $NC_2H_5$); m.p. 102° C. |
| 84 | JDL 491 | 3-butylcarbamylsulfonamido-4-isopropylaminopyridine (formula I : Z = isopropyl; $R_1$ = butylcarbamyl; $R_2$ = H and X = NH); m.p. 161° C. |
| 85 | JDL 384 | 3-propylcarbamylsulfonamido-4-(3'-chloro)-thiophenoxypyridine (formula I : Z = chlorophenyl; $R_1$ = propylcarbamyl; $R_2$ = H and X = S); m.p. 174–176° C. |
| 86 | JDL 385 | 3-tertiobutylcarbamylsulfonamido-4-(3'-chloro)-thiophenoxypyridine (formula I : Z = chlorophenyl; $R_1$ = t-butylcarbamyl; $R_2$ = H and X = S); m.p. 128° C. |
| 87 | JDL 528 | 3-sulfonamido-4-metatrifluoromethyl-thiophenoxypyridine (formula I : Z = metatrifluoromethylphenyl; $R_1$ = H; $R_2$ = H and X = S); m.p. 165° C. |
| 88 | JDL 529 | 3-butylcarbamylsulfonamido-4-metatrifluoromethylthiophenoxypyridine (formula I : Z = metatrifluoromethylphenyl; $R_1$ = butylcarbamyl; $R_2$ = H and X = S); m.p. 167–168° C. |
| 89 | JDL 530 | 3-cyclohexylcarbamylsulfonamido-4-metatrifluoromethylthiophenoxypyridine (formula I : Z = metatrifluoromethylphenyl; $R_1$ = cyclohexylcarbamyl; $R_2$ = H and X = S); m.p. 183–185° C. |
| 90 | JDL 531 | 3-p-chlorobenzoylsulfonamido-4-metatrifluoromethylthiophenoxypyridine (formula I : Z = metatrifluoromethylphenyl; $R_1$ = p-chlorobenzoyl; $R_2$ = H and X = S); m.p. 203–205° C. |
| 91 | JDL 532 | 3-propionylsulfonamido-4-metatrifluoromethylthiophenoxypyridine (formula I : Z = metatrifluoromethylphenyl; $R_1$ = propionyl; $R_2$ = H and X = S); m.p. 169–171° C. |
| 92 | L 2539 | 3-sulfonamido-4-(2-amino)-thiophenoxypyridine hydrochloride (formula I : Z = aminophenyl; $R_1$ = H; $R_2$ = H and X = S); m.p. 238–240° C. |

We claim:

[1. A compound of the following formula:

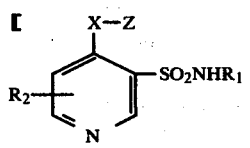

(1).]

in which

X represents an amino or $C_1$-$C_4$-alkylamino group;

$R_1$ represents a group of the formula:

$R_3NHCA$ (II), where A represents oxygen or sulfur and $R_3$ represents a $C_1$-$C_4$-alkyl, allyl, cyclohexyl, unsubstituted phenyl group or a phenyl group substituted by chloro, or a group of the formula $R_4CO$(III), wherein $R_4$ represents an unsubstituted phenyl group or a phenyl group substituted by chloro; $R_2$ represents hydrogen or a $C_1$-$C_4$-alkyl group, and Z represents a $C_1$-$C_4$-alkyl, methylfuryl, pyridyl or unsubstituted phenyl group, or a phenyl group substituted by one or two halogen atoms or by a $C_1$-$C_4$-alkyl, alkoxy, trifluoromethyl or nitro group, or by a trifluoromethyl group and a halogen atom with the provisos that:

1. when X represents an amino group, Z, $R_1$, $R_2$, $R_3$ and $R_4$ have all the above indicated meanings;
2. when X represents an alkylamino group, Z may only represent a $C_1$-$C_4$-alkyl group or a phenyl group as defined hereabove and $R_1$ may further represent a group of the formula:

$R_5CO$ (IV)

in which $R_5$ represents hydrogen or a $C_1$-$C_4$-alkyl group;

3. when X represents an amino group and Z is other than a phenyl group, $R_1$ may further represent hydrogen or a group of the formula (IV) as above defined, as well as a pyridine N-oxide of the compound of formula I and the pharmaceutically acceptable base and acid addition salts of said compounds.]

[2. 3-Ethylcarbamylsulfonamido-4-(3'-trifluoromethyl)-phenylaminopyridine-N-oxide.]

[3. 3-Isopropylcarbamylsulfonamido 4-(3'-methyl)-phenylaminopyridine-N-oxide.]

4. 3-Methylcarbamylsulfonamido-4-(3'-trifluoromethyl)-phenylaminopyridine.

5. 3-Ethylcarbamylsulfonamido-4-(3'-trifluoromethyl)-phenylaminopyridine.

6. 3-Isopropylcarbamylsulfonamido-4-(3'-chloro)-phenylaminopyridine.

7. 3-Methylcarbamylsulfonamido-4-(3'-methyl)-phenylaminopyridine.

8. A pharmaceutical composition [containing an anti-inflammatory, or] *comprising a* diuretic effective amount of a compound of claim 9 [and] *together with* a pharmaceutical carrier[or vehicle].

*9. A compound of the formula:*

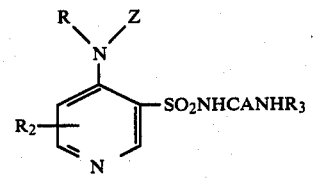

*in which:*

*R represents a hydrogen atom or a $C_1$-$C_4$ alkyl group;*

*$R_2$ represents a hydrogen atom or a $C_1$-$C_4$-alkyl group;*

*$R_3$ represents a $C_1$-$C_4$-alkyl, allyl, cyclohexyl, unsubstituted phenyl group or a phenyl group substituted by chloro;*

*A represents oxygen or sulfur; and*

*Z represents a $C_1$-$C_4$-alkyl, methylfuryl, pyridyl or unsubstituted phenyl group or a phenyl group substituted by one or two halogen atoms or by a $C_1$-$C_4$-alkyl, alkoxy, trifluoromethyl or nitro group or by a trifluoromethyl group and a halogen atom;*

*with the proviso that when R represents a $C_1$-$C_4$ alkyl group, Z may only represent a $C_1$-$C_4$ alkyl or a phenyl group as defined hereabove,*

*and the pharmaceutically acceptable base addition salts or acid addition salts of said compounds.*

*10. A compound according to claim 9, in which:*

*R represents hydrogen,*

*$R_3$ represents a $C_1$-$C_4$-alkyl group,*

*A represents oxygen, and*

*Z represents a $C_1$-$C_4$-alkyl group or a phenyl group as defined in claim 9.*

*11. 3-Isopropylcarbamylsulfonamido-4-(3'-methyl)phenyl-aminopyridine.*

*12. A pharmaceutical composition comprising a diuretic effective amount of the compound of claim 3 together with a pharmaceutical carrier.*

* * * * *

UNITED STATES PATENT AND TRADEMARK OFFICE

CERTIFICATE EXTENDING PATENT TERM
UNDER 35 U.S.C. § 156

PATENT NO. : Re. 30,633

DATED : June 2, 1981

INVENTOR(S) : Jacques E. Delarge et al.

PATENT OWNER : A. Christiaens S.A.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

FIVE YEARS from the original expiration date of the patent, April 19, 1994, with all rights pertaining thereto as provided by 35 U.S.C. § 156(b).

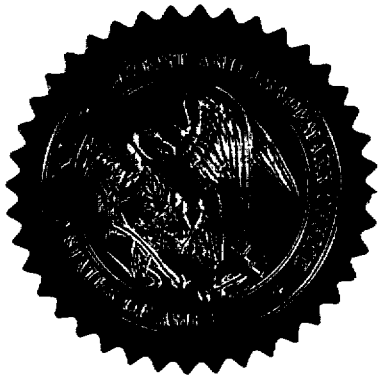

I have caused the seal of the Patent and Trademark Office to be affixed this 25th day of April 1996.

Bruce A. Lehman
Assistant Secretary of Commerce and
Commissioner of Patents and Trademarks